(12) United States Patent
Gershoni et al.

(10) Patent No.: US 10,329,075 B2
(45) Date of Patent: Jun. 25, 2019

(54) DISPENSER FOR VISCOUS CANNABIS FLUIDS AND MEANS THEREOF

(71) Applicant: Jetty Marketing, LLC, Wilmington, DE (US)

(72) Inventors: Ron Gershoni, Oakland, CA (US); Nathan Ferguson, Oakland, CA (US); David Eyvazzadeh, Denver, CO (US); Yuta Okkotsu, Aurora, CA (US); Ryan Artale, Crested Butte, CO (US)

(73) Assignee: JETTY MARKETING, LLC., Wilmington, DE (US)

( * ) Notice: Subject to any disclaimer, the term of this patent is extended or adjusted under 35 U.S.C. 154(b) by 0 days.

(21) Appl. No.: 15/977,187

(22) Filed: May 11, 2018

(65) Prior Publication Data

US 2018/0327173 A1 Nov. 15, 2018

Related U.S. Application Data

(63) Continuation of application No. 62/505,669, filed on May 12, 2017.

(51) Int. Cl.
| | | |
|---|---|---|
| *A61J 1/00* | (2006.01) | |
| *A61M 11/00* | (2006.01) | |
| *B05C 17/01* | (2006.01) | |
| *B65D 83/00* | (2006.01) | |
| *A24F 47/00* | (2006.01) | |

(52) U.S. Cl.
CPC .......... *B65D 83/0011* (2013.01); *A61J 1/00* (2013.01); *A61M 11/006* (2014.02); *B05C 17/0133* (2013.01); *A24F 47/002* (2013.01); *A24F 47/004* (2013.01)

(58) Field of Classification Search
CPC .......... B65D 83/0011; B05C 17/0133; A61M 5/31593; A61M 5/31585; A61M 2005/3104
See application file for complete search history.

(56) References Cited

U.S. PATENT DOCUMENTS

| | | | | |
|---|---|---|---|---|
| 2,052,296 | A * | 8/1936 | Huntley | B65D 83/0011 222/390 |
| 2,199,877 | A * | 5/1940 | Cervera | A46B 5/0095 132/311 |
| 4,136,801 | A * | 1/1979 | Pavenick | B65D 83/0011 222/105 |
| 8,540,124 | B2 * | 9/2013 | Francavilla | B65D 83/0011 222/386 |
| 9,717,859 | B2 * | 8/2017 | Harms | A61M 5/31511 |
| 9,914,580 | B1 | 3/2018 | Siciliano et al. | |
| 2004/0199117 | A1 * | 10/2004 | Giambattista | A61M 5/31551 604/134 |
| 2004/0260247 | A1 * | 12/2004 | Veasey | A61M 5/31551 604/207 |

(Continued)

*Primary Examiner* — Nicholas J. Weiss
(74) *Attorney, Agent, or Firm* — Voz Patents, LLC

(57) ABSTRACT

The present invention is directed to a dispensing device for the dispensation of a fluid substance. Aspects of the present invention include dispensing a viscous fluid in a measurable and repeatable manner with a single hand. The dispenser of the present invention can be used for a number of intended purposes including use with viscous fluids such as those associated with cannabis or tobacco consumption.

13 Claims, 13 Drawing Sheets

(56) References Cited

U.S. PATENT DOCUMENTS

| | | | |
|---|---|---|---|
| 2005/0283115 A1* | 12/2005 | Giambattista | A61M 5/3202 604/110 |
| 2007/0016142 A1* | 1/2007 | Burren | A61M 5/24 604/207 |
| 2007/0244436 A1* | 10/2007 | Saiki | A61M 5/31511 604/131 |
| 2008/0306446 A1* | 12/2008 | Markussen | A61M 5/20 604/139 |
| 2009/0247960 A1* | 10/2009 | Kohlbrenner | A61M 5/20 604/232 |

* cited by examiner

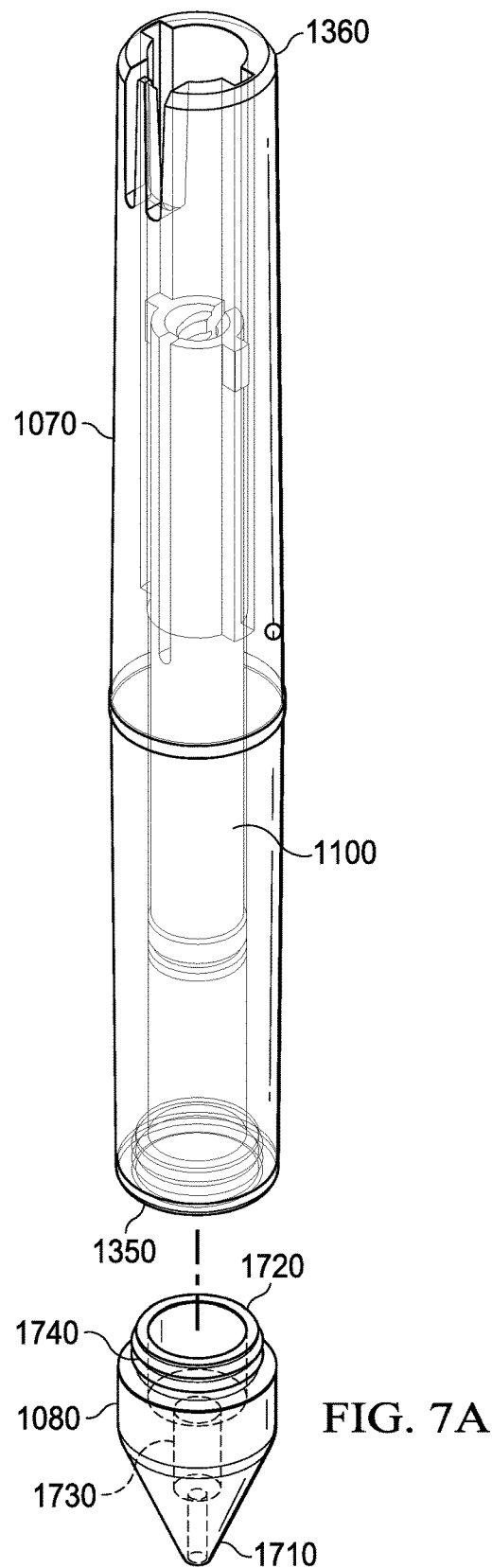
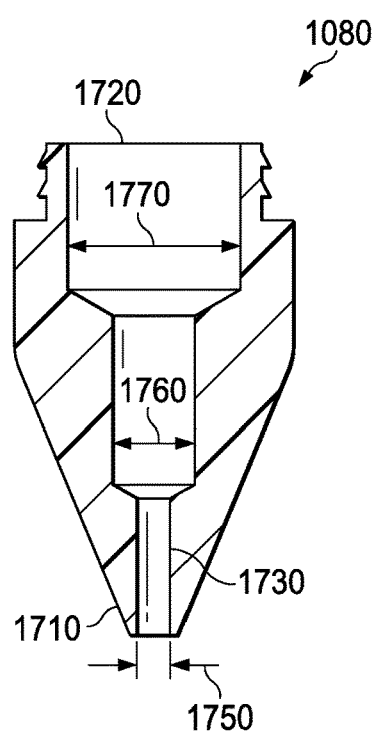
FIG. 7A
FIG. 7B

DISPENSER FOR VISCOUS CANNABIS FLUIDS AND MEANS THEREOF

CROSS REFERENCE TO RELATED APPLICATIONS

This application claims the benefit of currently pending U.S. provisional patent application 62/505,669 entitled "DISPENSER FOR VISCOUS CANNABIS FLUIDS AND MEANS THEREOF," filed May 12, 2017—the entire contents of which are incorporated herein by reference in its entirety for all purposes.

FIELD OF THE INVENTION

The present invention pertains to a dispenser and means thereof for dispensing cannabis concentrate to a vaporization system. More particularly, the dispenser of the present invention is a one-handed controlled dispenser device for viscous cannabis fluids.

BACKGROUND OF THE INVENTION

Cannabis plants have been used for thousands of years for a multitude of reasons. Some common uses include ceremonial, medicinal, and recreational purposes. Over time, the plant has been synthesized into different forms. For example, some cannabis plants are dried and smoked, it is cooked into foods and candy to be ingested, and others create an extract of liquid cannabis concentrate.

Cannabis concentrate can refer to multiple forms of cannabis such as a cannabis extract in a fluid, viscous, or wax like substance that can be vaporized, a liquid tincture that is placed under the tongue, or an orally-administered cannabis oil that does not contain the psychoactive compound tetrahydrocannabinol.

To utilize cannabis concentrate extract, the concentrate is traditionally transferred from its storage container to a system that vaporizes the cannabis concentrate. This process, known to some as dabbing, typically uses a dentistry like tool for scraping the wax like substance to an extremely hot object (sometimes referred to as a rig), then inhaling the vapors that are produced. In use, a rig may reach temperatures of anywhere up to 537° C. (1000° F.). Others may use a syringe like tool to transfer the concentrate to a preheated object and inhale the vapors that are produced.

Transferring the cannabis concentrate to another system, however, can be difficult. For example, the concentrate typically has sticky or tacky physical characteristics that make transfer cumbersome. Therefore, a tool is needed to transfer the concentrate to another system for use.

In the cannabis industry, there are a variety of tools or devices used to dispense liquid cannabis concentrate.

SUMMARY OF THE INVENTION

The present invention as disclosed herein surrounds a dispensing apparatus for fluid. In certain embodiments, the present invention allows one-handed actuation in dispensing fluid cannabis concentrate. Certain existing solutions for the dispensing of such fluids are not able to completely evacuate a reservoir holding the fluid, wasting the unused fluid. It is an aspect of the present invention to permit the complete evacuation of the reservoir little or no remaining concentrate in the dispenser that would otherwise go wasted. It is a further intended aspect of the present invention to allow the reverse operation of a dispensing. The reverse operation allows a user to stop dispensing mid-use if the user elects not to dispense less fluid.

Many known dispensing devices used in conjunction with a vaporization system, however, are difficult to handle and operate at the same time. Dispensing devices often require the use of two hands to dispense the fluid contained within the device. For instance, when using the dispenser, the dispenser requires one hand to hold or stabilize the dispenser at the same time the second hand engages the dispenser mechanism to dispense the liquid concentrate. During this process to dispense the liquid, both hands are engaged with the dispenser and there is not a convenient way to also hold, stabilize, or use the vaporization system that the liquid is being dispensed to for ultimate use. Therefore, a previously unsolved problem is need for a simple and easy dispensing device that only requires one hand to dispense the liquid contained inside the device to allow the second-hand freedom of use.

In some existing solutions, the dispenser tip in relation to the object that pushes, forces, or ejects the liquid out of the dispenser does not allow for the liquid to be completely dispensed from the dispenser. Therefore, a portion of the cannabis concentrate liquid remains trapped inside the dispenser and the user is unable to access and use the valuable remaining cannabis concentrate. Thus, another previously unsolved problem is need for a dispensing device that dispenses all the liquid from the dispenser and does not leave any liquid inside the device to go to waste.

Liquid cannabis concentrate can have various consistencies and some concentrates are more viscous than others. Because of the viscous property of some cannabis concentrates, the liquid is slow-moving inside the dispenser. Therefore, the liquid will not immediately be ejected from the dispenser when the mechanism is enacted, but instead it will ooze slowly from the dispenser. In other known dispensing devices, the devices only allow the mechanism inside the device to force the liquid out to be dispensed and do not allow the mechanism to be retracted. If the mechanism is retracted before the viscous concentrate is dispensed, however, it would allow the concentrate to remain inside the dispenser for later use. Therefore, a formerly unsolved problem is need for a dispenser that can retract or back up the mechanism that produces the dispensing action of the liquid.

Another know dispensing device is a syringe. Syringes are traditionally used to dispense fluid substances, but syringes are inconvenient and challenging to control. It is difficult for most to use one hand to activate a syringe and dispense the fluid while simultaneously trying to control the amount of fluid being dispensed to a vaporization system. The amount of fluid dispensed from a syringe is determined by how much the user pushes and it does not allow the user to predetermine how much to dispense. Furthermore, the use of a syringe has a stigma surrounding it due to illegal use of syringes in the use of narcotics. It therefore remains a long felt and unmet need to provide a means for a simple and easy to use one-handed fluid cannabis concentrate dispenser.

The fluid cannabis concentrate dispenser of the present invention has a general mechanism of first twisting to engage the mechanism and second a push down release to dispense the internal fluid. The dispenser includes a chamber body, a twisting sleeve, a lead-screw, a plunger, a dispensing tip, and a cap.

The user employs the dispenser, which is pre-filled with fluid, by first removing the cap. The cap has an internal stopper inside the cap which indexes into the hole of the dispensing tip to prevent leaking of fluid when the cap is installed on the dispensing apparatus. Next, the user twists the twisting sleeve. The twisting action results in a clicking that provides tactile and audio feedback to the user. In addition, the twisting pushes one end of the lead-screw out of the end of the dispenser to extend a push-button. The user holds the dispenser in one hand and pushes the push-button on the dispenser with a finger. The pressing of the push-button which actuates the plunger within the chamber body to apply pressure on the fluid within an internal reservoir to dispense the fluid from the dispensing tip.

An object of the present invention is to dispense fluid using a device that only requires one hand to operate, through the two-step mechanism of twisting and then enabling time to pause to have freedom of one hand and the device in one hand and releasing the fluid via a push-button.

Another object of the present invention is to provide a user with a convenient way to carry, transfer, and dispense fluid cannabis concentrate, through the simple and easy to use handheld device that does not require the user to handle the concentrate and the user does not have to worry about leakage.

Another object of the present invention is to provide a dispenser that allows the user the option to back up the plunger if the user no longer wishes to dispense the fluid. Backing up the plunger places a negative pressure on the reservoir and may further allow the retraction of the fluid away from the dispensing tip, further preventing leakage. Because the plunger is not prevented from moving in either direction inside the main chamber body, it provides the user flexibility.

Another object of the present invention is to provide a dispenser that allows all the fluid inside the main chamber body to be dispensed from the device to prevent waste of fluid that would otherwise be trapped inside the dispenser tip.

Some existing fluid dispensing apparatuses have a plastic tip for the dispensing of fluid. Such solutions fail if they come into contact with a hot rig. Contact with an extremely hot object during use can result in the melting of the plastic tip resulting in damage to the dispenser, potential damage to a rig, and potential release of chemicals from the burning of plastic. It is an aspect of certain embodiments of the present invention to comprise a thermally resistant tip. In certain embodiments, the thermally resistant tip comprises a thermally resistant material such as aluminum. It will be appreciated that a thermally resistant tip surrounds a tip that is able to withstand operational temperatures of a rig without permanent deformation. Aluminum, for instance, has a melting temperature of 660° C. (1221° F.).

A problem with some existing dispensers for dispensing a fluid, such as cannabis extract, is that are prone to unintentional misuse and consumption by children. Studies have shown in some cases that excessive exposure to cannabinoid stimulation during early phases of development may result in the alteration of normal development of certain neural systems. Unintentional consumption by children may also result in breathing problems or increased heart-rate in certain cases. In such cases, a child is typically admitted to the emergency room for medical attention.

It is an object of certain embodiments of the present invention to provide a child-safety feature which mitigates the unintentional consumption of an extract by a child. A child-safety feature of certain embodiments surrounds the locking of a cap the tip of a dispenser. In certain embodiments, a child-safety feature comprises a cap that can be unlocked and subsequently removed when indicia of the cap and the tip are aligned. It will be appreciated however, that a child-safety feature is not limited to such embodiments. It will be appreciated to those skilled in the art that a child-safety feature comprises mechanisms known to those skilled in the art, including a "palm-N-turn" mechanism. It will be further appreciated that a child-safety feature are mechanisms which are in compliance with standards such as ISO 8317 "Child Resistant Packaging—Requirements and testing procedures for reclosable packages", ISO 13127 "Packaging—Child resistant packaging—Mechanical test methods for reclosable child resistant packaging systems," or ASTM D3475 "Standard Classification for Child-Resistant Packages."

Embodiments of the invention provide functionality for the ease of assembly of the apparatus. For instance, the plunger includes a female threaded feature for the threaded engagement of a threaded male portion of the lead-screw. For the ease of assembly, the female threaded feature may further include features allowing the deflection of a distal portion of the female threaded feature. The deflection of a distal portion of the female threaded feature allows the lead-screw to be inserted directly into the female threaded feature without the need to spin the lead-screw to advance the lead-screw into the plunger.

BRIEF DESCRIPTION OF THE DRAWINGS

FIG. 1B—A perspective view of certain embodiments of a dispensing apparatus

FIG. 7A—An exploded perspective view of certain embodiments of a plunger, plunger tip, chamber body and dispensing tip FIG. 7B—A cross-sectional view of certain embodiments of a dispensing tip FIG. 8A—An assembled side view of certain embodiments having a child-safety feature FIG. 8B—A disassembled side view of certain embodiments having a child-safety feature FIG. 8C—An exploded perspective view of certain embodiments having a child-safety feature

DETAILED DESCRIPTION

Figure 1A:
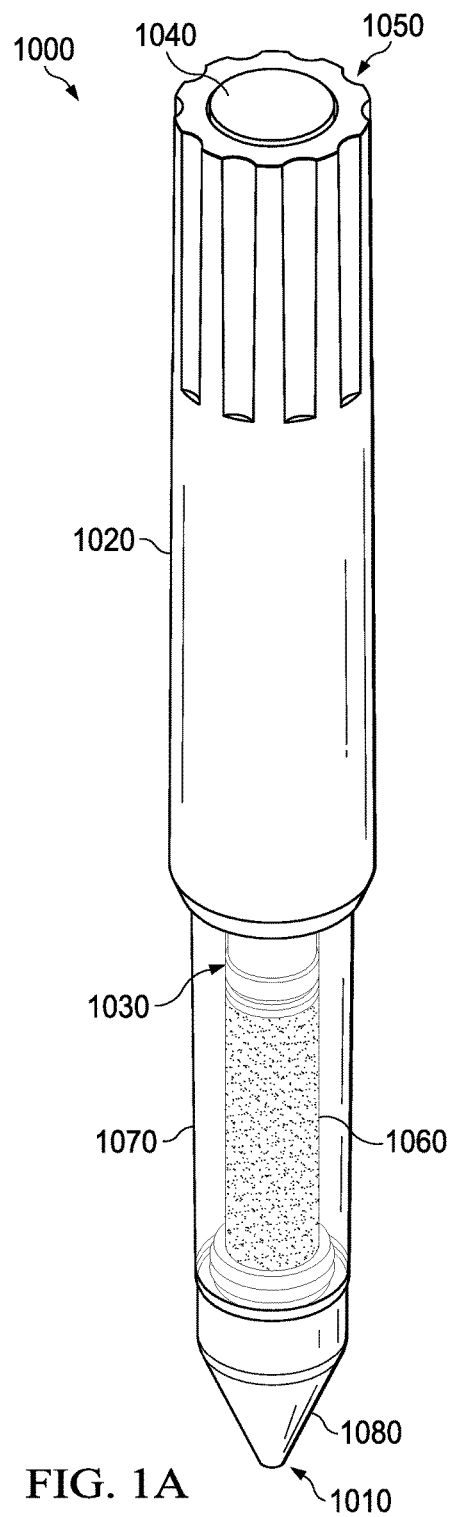
FIG. 1A—A perspective view of certain embodiments of a dispensing apparatus
Figure 1B:
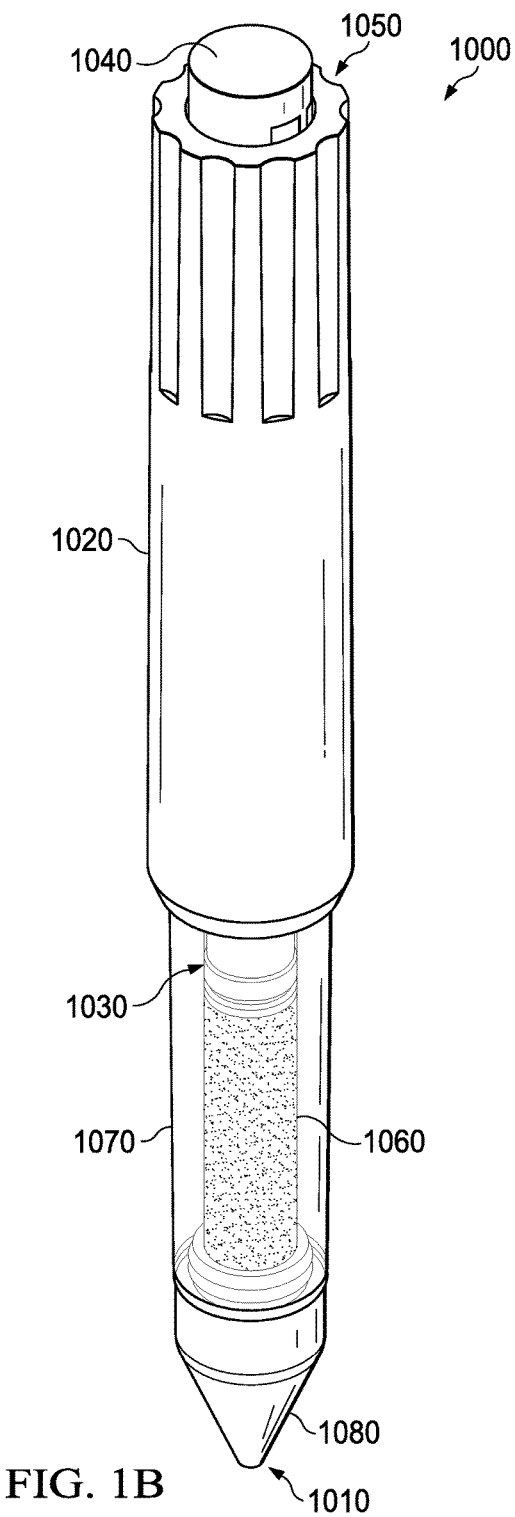

Certain embodiments of the invention surround a dispensing apparatus 1000, as shown in FIG. 1A and FIG. 1B, for the dispensing of a viscous cannabis fluid from a first end 1010 of the dispensing apparatus 1000 for consumption by an individual surrounding a number of intended consumption practices. Certain embodiments of the present invention as disclosed are directed toward a dispensing apparatus 1000 allowing single-hand usage with mechanisms for pre-loading of the dispensing apparatus 1000 through the actuation of a twisting sleeve 1020. In such cases, the actuation of a twisting sleeve 1020 elongates a plunger assembly 1030, extending a push-button 1040 from a second end 1050 of the apparatus. Depressing the extended push-button 1040 advances the plunger assembly 1030, applying pressure on a reservoir 1060 within a chamber body 1070. The reservoir 1060 holds a viscous fluid 1080, the application of pressure dispenses the viscous fluid from the chamber body 1070 and through a dispensing tip 1080 at a first end of the dispensing apparatus 1000.

Figure 2A:
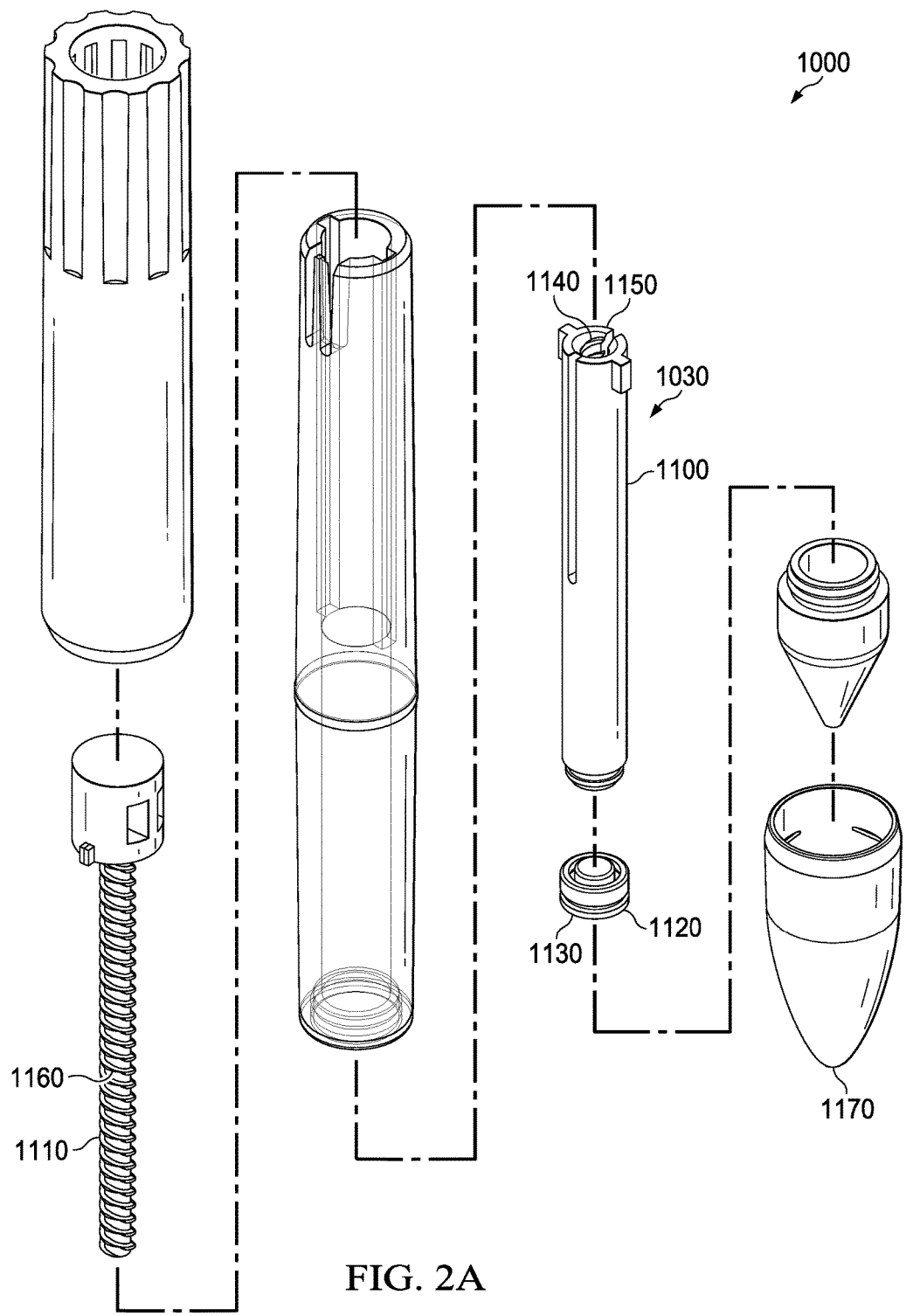
FIG. 2A—An exploded perspective view of certain embodiments of a dispensing apparatus FIG. 2B—A cross-sectional side-view of certain embodiments of a dispensing apparatus FIG. 3A—An exploded perspective view of certain embodiments of a dispensing apparatus FIG. 3B—An exploded perspective view of certain embodiments of a plunger assembly FIG. 4A—An exploded perspective view of certain embodiments of a plunger, plunger tip and chamber body FIG. 4B—A cross-sectional side-view of certain embodiments of a plunger assembly and chamber body FIG. 4C—An exploded cross-sectional perspective view of certain embodiments of a dispensing apparatus FIG. 5—An exploded cross-sectional perspective view of certain embodiments of a dispensing apparatus FIG. 6A—An exploded cross-sectional view of certain embodiments of a dispensing apparatus FIG. 6B—A cross-sectional side-view of certain embodiments of a dispensing apparatus (dispensing tip not shown)

Certain embodiments of a dispensing apparatus 1000, as shown in FIG. 2A, comprise a plunger assembly 1030 having a plunger 1100 and a lead-screw 1110. In such embodiments the plunger 1100 comprises an elongated body of constant cross-sectional profile having a plunger tip 1120 at a first end 1130 and a female threaded feature 1140 at a second end 1150. In such embodiments the plunger assembly 1030 further comprises a lead-screw 1110 having male threading 1160 for engaging with the female threaded feature 1140. In certain embodiments the female threaded feature 1140 and the lead-screw 1110 have right-hand threads, while other embodiments use left-hand threads.

Figure 2B:
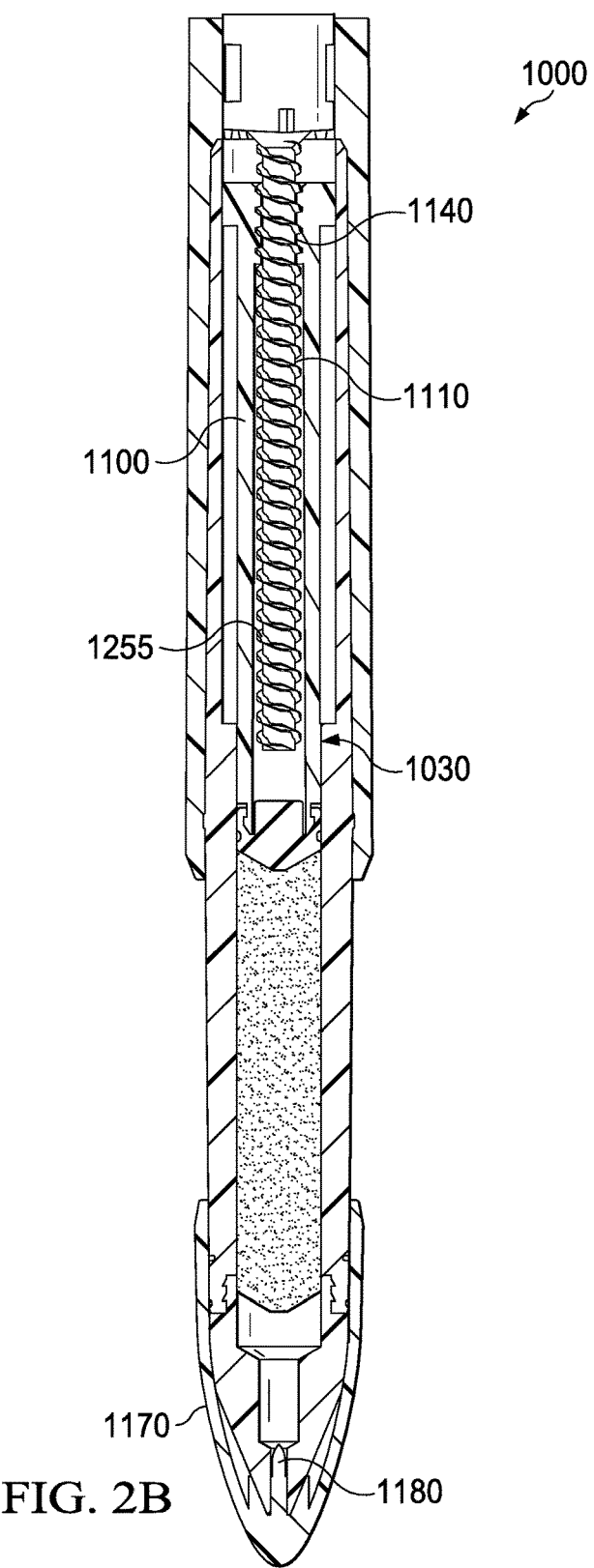

Certain embodiments of a dispensing apparatus 1000, shown in FIG. 2B, comprise a lead screw 1110 having thread step features 1255. Such thread step features 1255 engage with female threaded features 1140 of a plunger 1100 when a lead screw 1110 and plunger 1100 are assembled in a plunger assembly 1030. The engagement between the thread step features 1255 and female threaded features 1140 serves to prevent unintended rotation of a lead screw 1110 in relation to a plunger 1100 when axial force is applied to the lead screw 1110 to advance the plunger 1100 to dispense a fluid.

Certain embodiments of a dispensing apparatus 1000, as shown in FIG. 2A and FIG. 2B, comprise a cap 1170 with an open end for disposing over the first end 1010 of the apparatus. In some embodiments, the cap 1170 further comprises an internal stopper 1180. In such embodiments, the internal stopper 1180 comprises an elongated form configured to be disposed into pathway 1730 of a dispensing tip 1080, shown in FIG. 7B. The installation of the cap 1170, once again referencing FIG. 2A, serves to prevent undesired dispensing of extract when the dispensing apparatus 1000 is not in use.

Figure 3A:
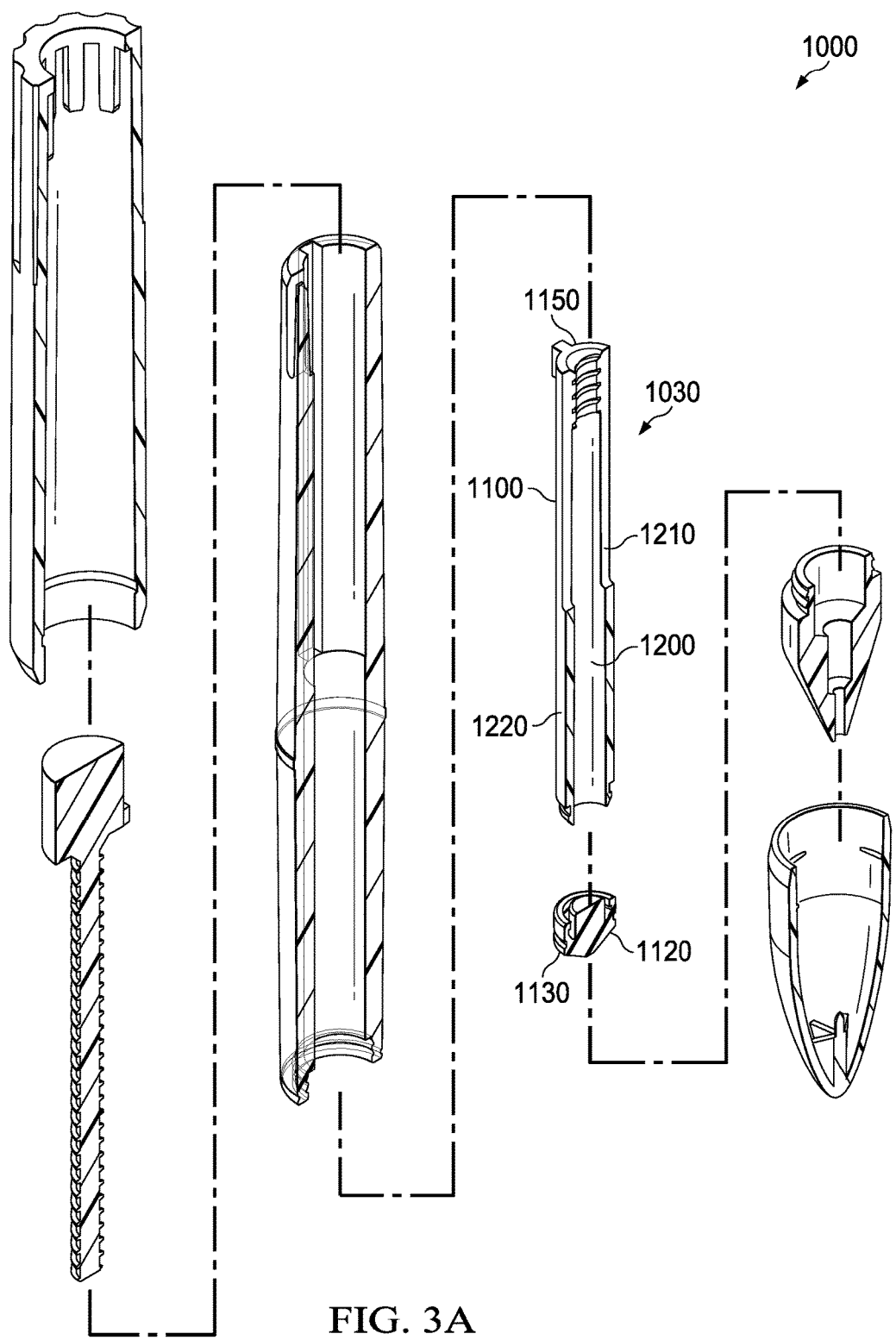
Figure 3B:
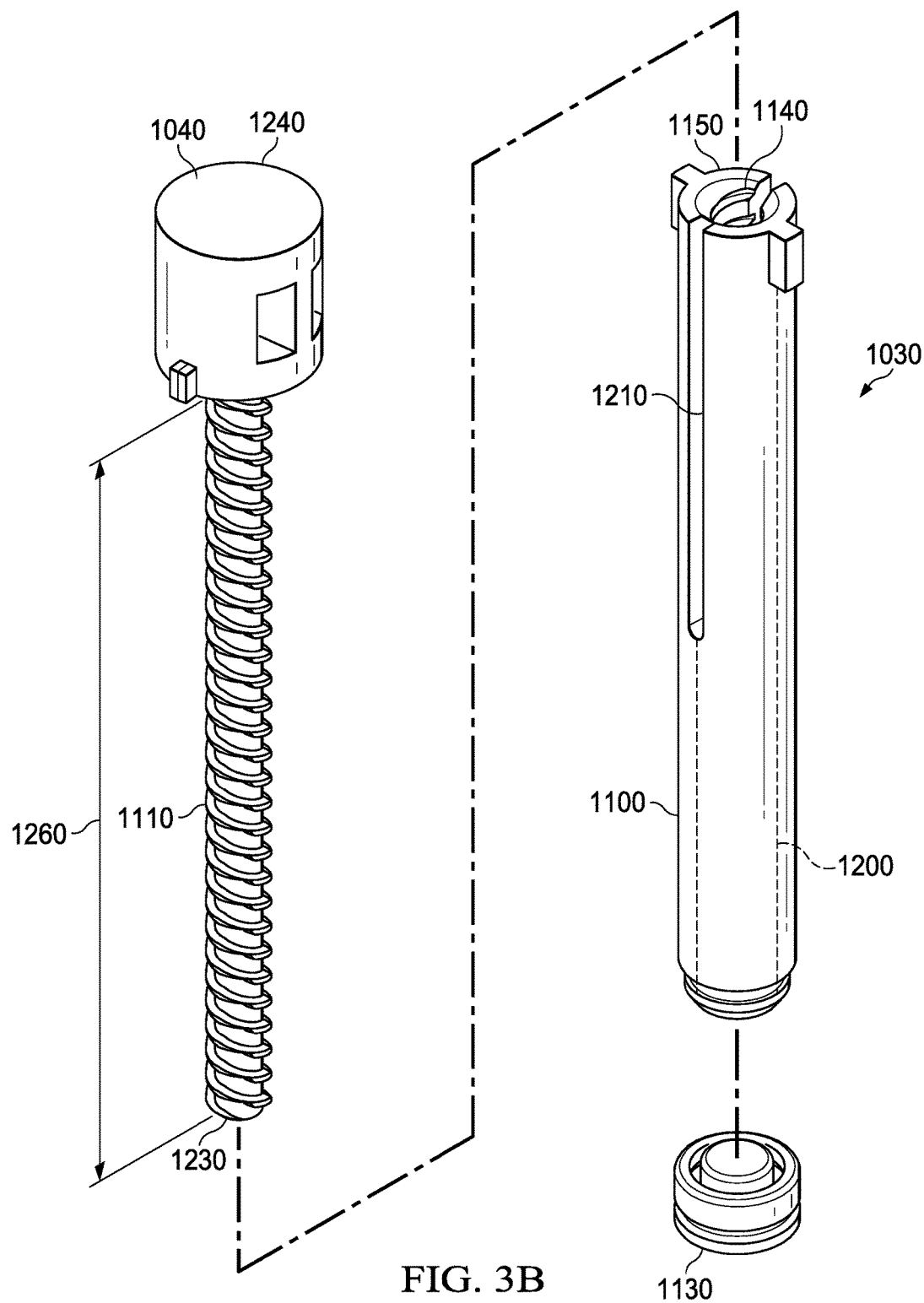

Certain embodiments of a dispensing apparatus 1000, as seen in FIG. 3A, comprise a plunger assembly 1030 having a plunger 1100 further comprising an elongated body of constant cross-sectional profile, such as but not limited to a cylindrical profile. Such plunger 1100 has a hollow form with a closed first end 1130 and an open second end 1150. The first end 1130 of the plunger further comprises a plunger tip 1120 while the second end 1150 comprises an axial bore 1200 extending from the second end 1150 to a location proximate to the first end 1130. In other embodiments, the axial bore 1200 extends through the first end 1130 of the plunger and the first end 1130 is closed by the plunger tip 1120. The plunger further comprises a slot 1210 through an external surface 1220 of the plunger to 1100 the axial bore 1200, extending from the second end 1150 of the plunger toward the first end 1130 of the plunger and terminating therebetween. Certain embodiments of a plunger 1100, referencing FIG. 3B, comprise a plurality of slots 1210. A slot 1210, as used in such an embodiment allows for the outward deflection of the second end 1150 of the plunger when a mating element, such as a lead-screw 1110 is inserted into the axial bore 1200 in the open second end 1150 of the plunger 1100. The axial bore 1200 of the plunger 1100 further comprises a female threaded feature 1140 extending from a location proximate to the second end 1150 of the axial bore 1200 toward the first end 1130 of the plunger. The female threaded feature 1140 of such an embodiment has a length less than the length of the slot 1210. In such embodiments, the plunger assembly 1030 further comprises a lead-screw 1110 having a first end 1230, a second end 1240, and male threading 1160 extending therebetween. In certain embodiments, the length 1260 of the lead-screw is equal to the length 1270 of the axial bore of the plunger. However the length 1260 of the lead-screw may be longer or shorter of the length 1270 of the axial bore if desired. In certain embodiments the length 1260 of the lead-screw is 4.64 cm (1.83 in). In certain embodiments, the lead-screw 1110 features a push-button 1040 affixed to the second end 1240 of the lead-screw. Such a push-button 1040 has a consistent cross-sectional profile, such as but not limited to a cylindrical profile.

Figure 4A:
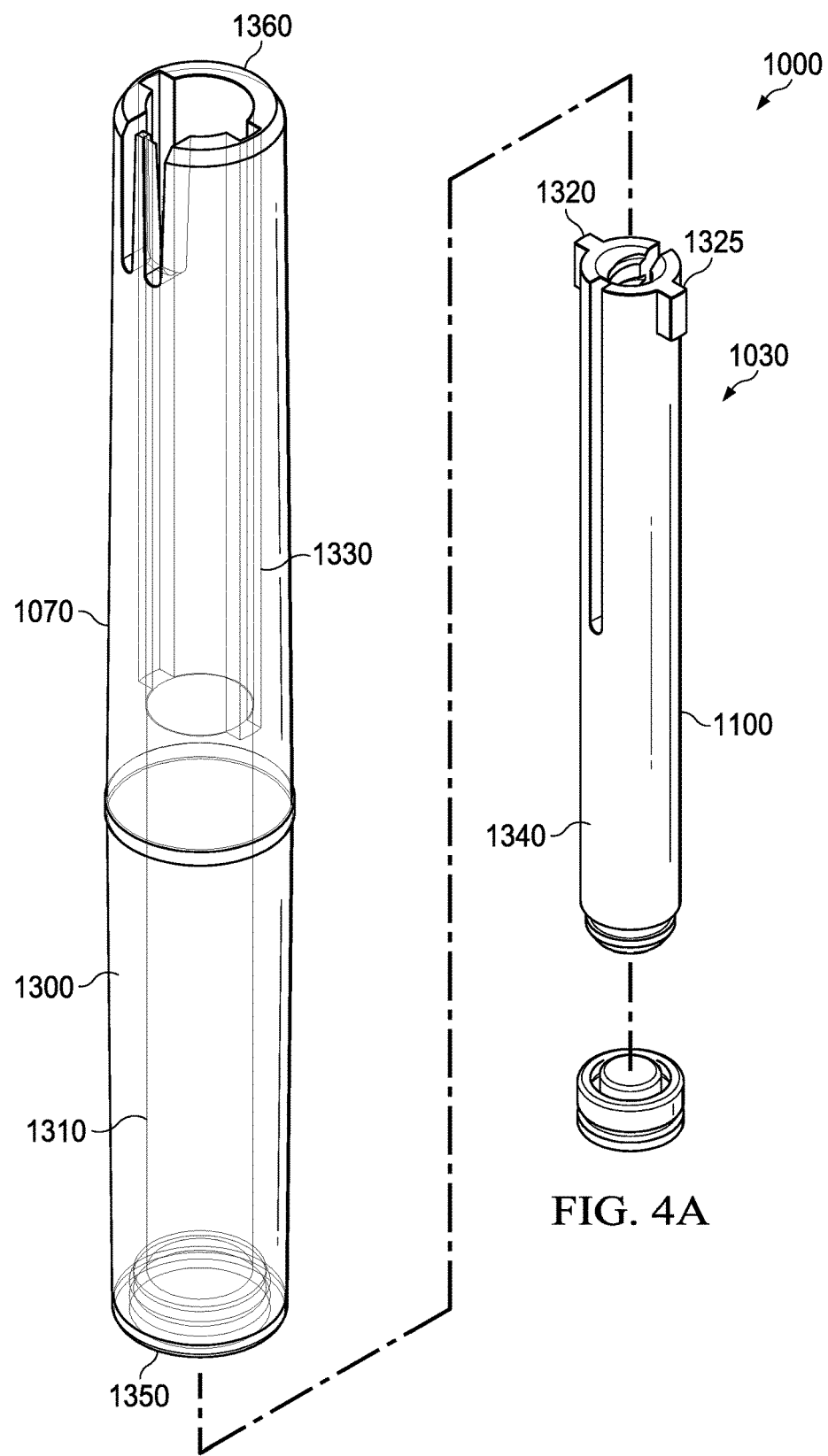

Certain embodiments of a dispensing apparatus 1000, shown in FIG. 4A, comprise a plunger assembly 1030 and a chamber body 1070. The chamber body 1070 of such embodiments comprises an external surface 1300 cylindrical external cross-sectional profile and an internal surface 1310 having a cylindrical internal cross-sectional profile which a plunger 1100 can be slidably inserted into. In certain embodiments, the plunger 1100 further comprises anti-spin features 1320 which engage with a channel 1330 of the chamber body. In certain embodiments, the anti-spin feature 1320 comprises a tab feature 1325 extending radially away from an external surface 1340 of the plunger. Some embodiments of an anti-spin feature 1320 are near, or coincident with, the second end 1150 of the plunger. It may be desired to use one, or a plurality of such tab features 1325. In such an embodiment, the chamber body 1070 further comprises a channel 1330 disposed in the internal surface 1310 of the chamber body extending from the second end 1360 of the chamber body toward the first end 1350 of the chamber body.

Figure 4B:
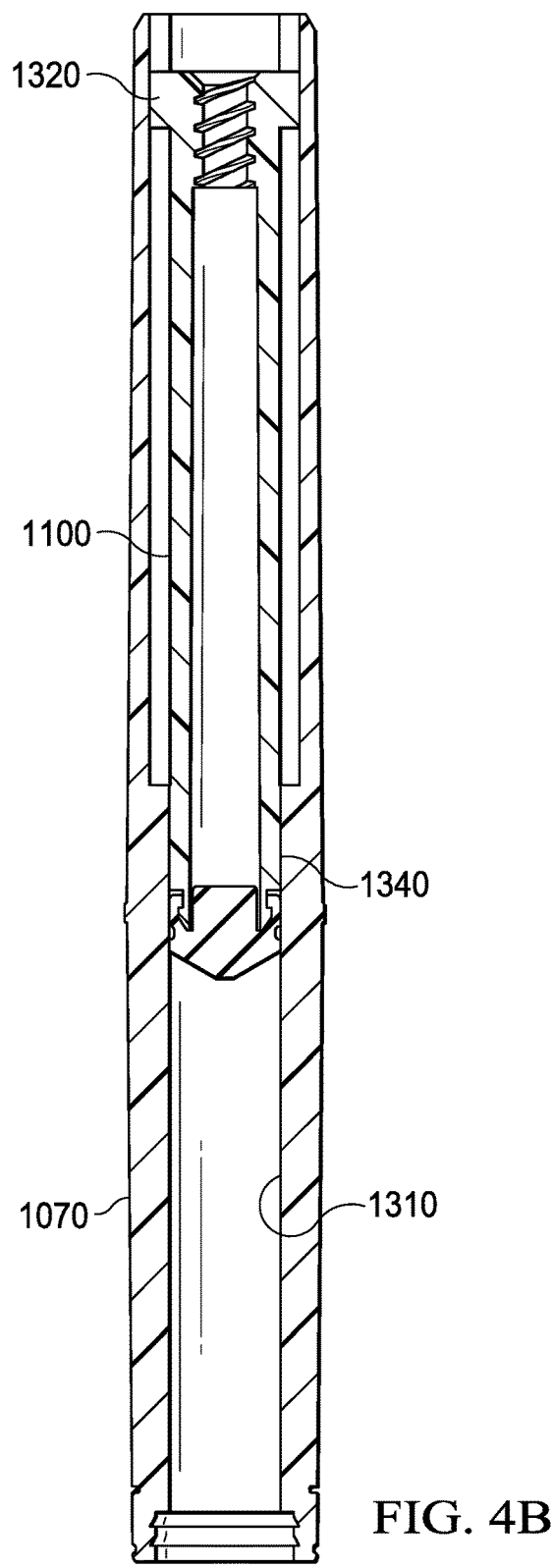

It will be appreciated that an anti-spin feature 1320, as seen in FIG. 4B is intended to prevent the spinning of a first element of the present invention in relation to a second element of the present invention. It will be further appreciated that in the case of a plunger 1100 and chamber body 1070, such an anti-spin feature 1320 comprises a plunger 1100 which indexes into a chamber body 1070. This may be accomplished in a variety of strategies including, but not limited to, a plunger 1100 having a cross-sectional profile of a non-cylindrical external surface 1340 and the internal surface 1310 of a chamber body having a complimentary internal surface 1310 profile. This allows the plunger 1100 to move axially within such a chamber body 1070, but not rotatively in relation to the chamber body 1070.

Figure 4C:
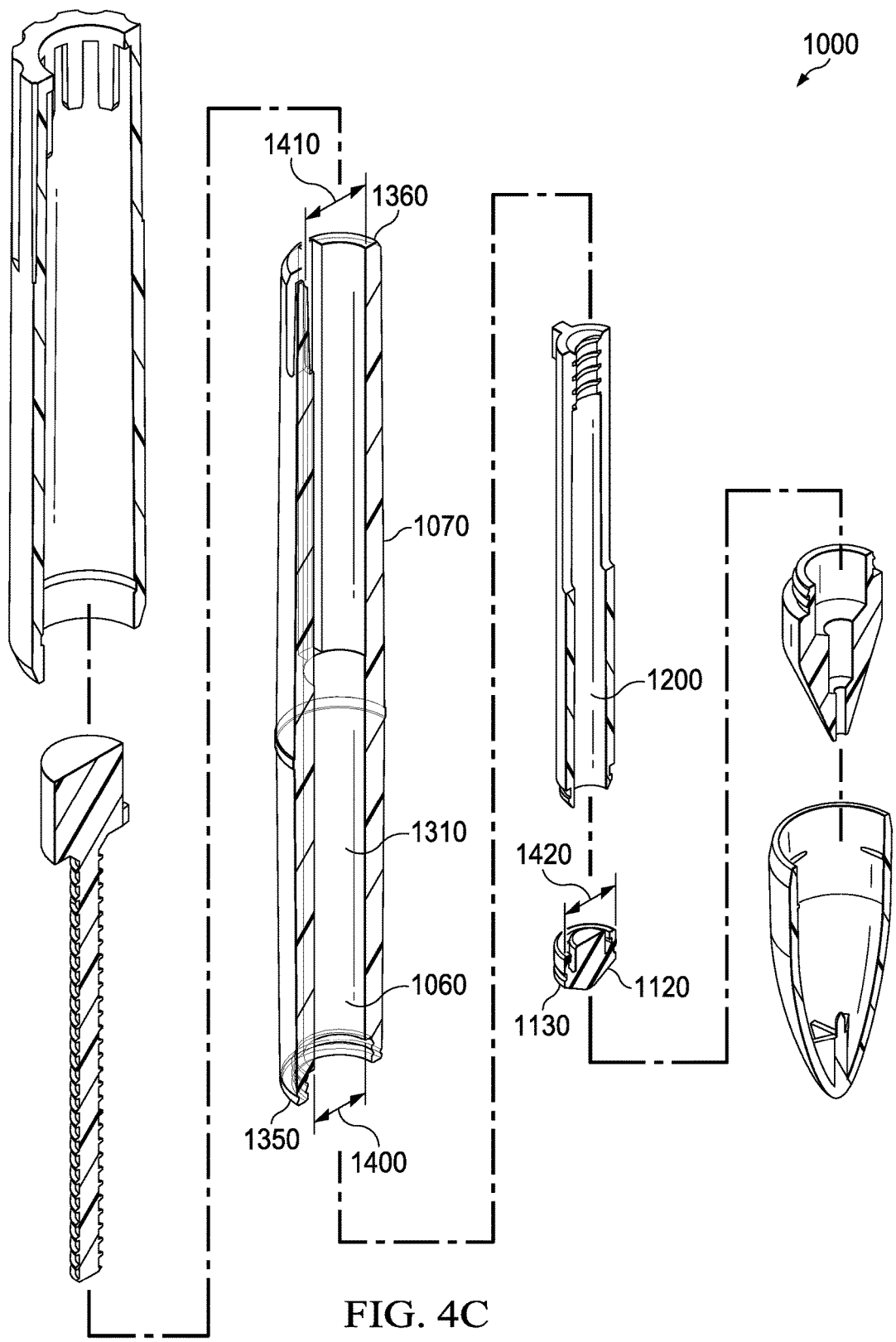

Certain embodiments of a dispensing apparatus 1000, as seen in FIG. 4C, comprise a chamber body 1070 having an axial bore 1200 having a first diameter 1400 and a second diameter 1410. The first diameter 1400, consistent with a reservoir 1060 in the chamber body 1070, is equal to or less than a maximum diameter 1420 of a plunger tip 1120 disposed at the first end 1130 of a plunger. This second diameter 1410 is consistent with or proximate to the first end 1350 of the chamber body. The second diameter 1410, consistent with a second end 1360 of a chamber body is equal to or greater than the maximum diameter 1420 of the plunger tip. In other embodiments, it may be desired that the second diameter 1410 be equal to or less than the maximum diameter 1420 of the plunger tip 1120. In such embodiments that the first diameter 1400 or second diameter 1410 of the chamber body are less than or equal to the maximum diameter 1420 of the plunger tip while in other embodiments the first diameter of the axial bore is greater than the maximum diameter 1420 of the plunger tip. It will be appreciated that it may be desired to manufacture the plunger tip 1120 from an elastic or semi-elastic material to allow for the plunger tip 1120 to be slidably inserted into the chamber body 1070 while creating a seal between the plunger tip 1120 and an internal surface 1310 of the chamber body. In certain embodiments the first diameter 1400 of the chamber body is 0.635 cm (0.250 in), and the second diameter 1410 of the chamber body is 0.645 cm (0.254 in). In certain embodiments the maximum diameter 1420 of the plunger tip is 0.632 cm (0.249 in) while in other embodiments the maximum diameter 1420 of the plunger tip is 0.638 cm (0.251 in).

Figure 5:
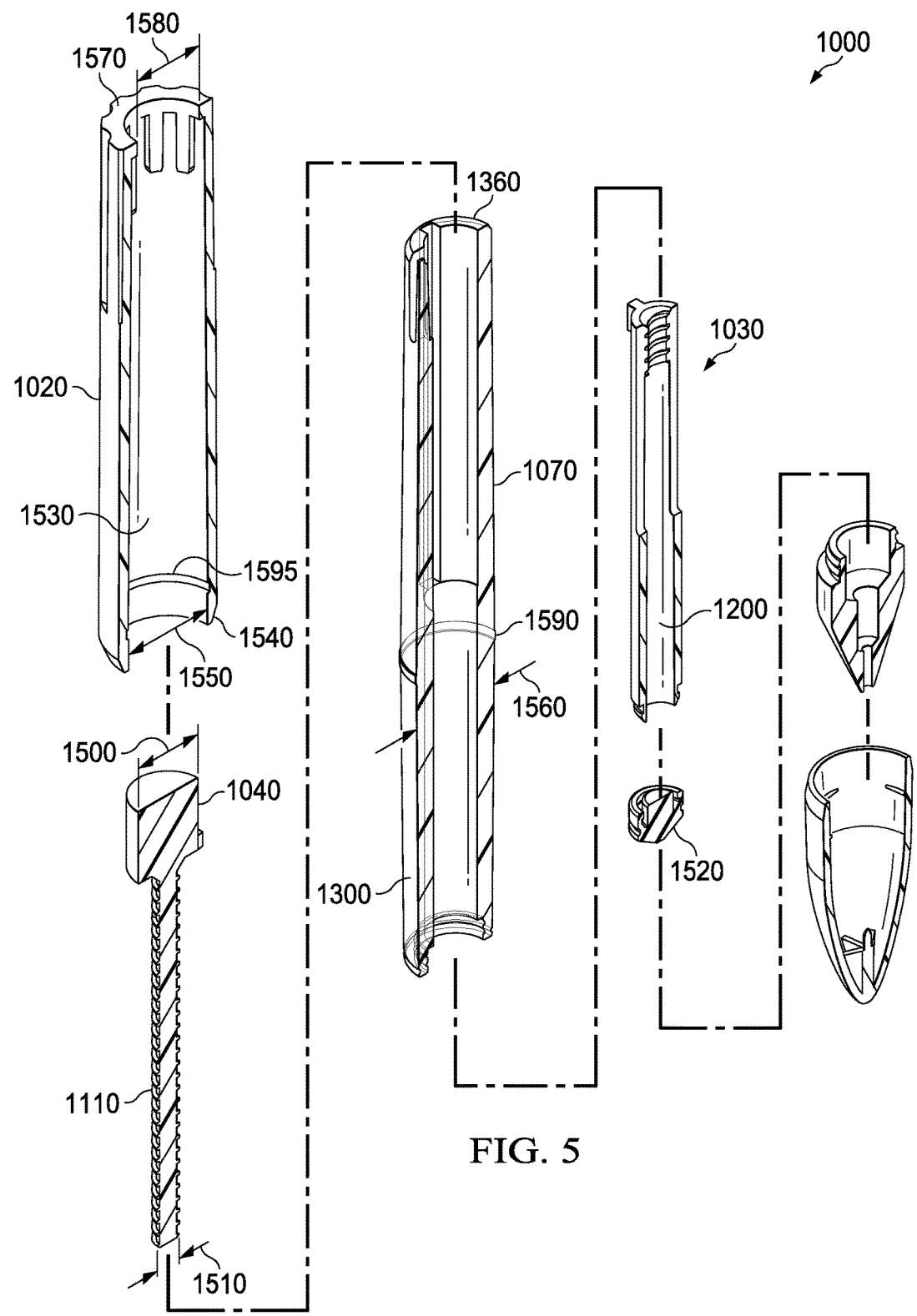

Certain embodiments of a dispensing apparatus 1000 as disclosed comprise a plunger assembly 1030, a chamber body 1070 and a twisting sleeve 1020 as seen in FIG. 5. The plunger assembly 1030, further comprises a lead-screw 1110 with a push-button 1040, and the push-button 1040 has a larger diameter 1500 than the lead-screw diameter 1510. The diameter 1500 of the push-button is also larger than the second diameter 1410 of the axial bore 1200 of the plunger in such embodiments. The plunger assembly 1030 has a first end 1520 inserted through the second end 1360 of the chamber body. The twisting sleeve 1020, has a cylindrical bore 1530 having: a first open end 1540 with internal diameter 1550 equal to or greater than the external diameter 1560 of the chamber body and a second open end 1570 with internal diameter 1580 equal to or greater than the push-button diameter 1500. In certain embodiments the twisting sleeve 1020 is configured to be slidably disposed over the second end 1360 of the chamber body such that the push-button 1040 may extend through the second open end 1570 of the twisting body. It may be desired for the chamber body 1070 to further comprise first engagement feature 1590 on the external surface 1300 of the chamber body, and the twisting sleeve 1020 to feature a second engagement feature 1595 in the cylindrical bore 1530 of the twisting sleeve. In such cases, the mating of a first engagement feature 1590 and the second engagement feature 1595 constrains axial movement between the twisting sleeve 1020 and the chamber body 1070 but allows independent rotation of the chamber body 1070 and the twisting sleeve 1020 with respect to each other.

In certain embodiments, shown in FIG. 5, the large-diameter 1500 of the push-button is 8.41 mm (0.3311 in), the internal diameter 1550 of the first open end of the twisting sleeve is 11.2 mm (0.4414 in), the internal diameter 1580 of the second open end of the twisting sleeve is 8.87 mm (0.3492 in), the external diameter 1560 of the chamber body is 10.5 mm (0.4123 in), the third diameter 1770 (FIG. 7B) of the pathway of the dispenser tip and the maximum diameter 1420 of the plunger tip are 6.33 mm (0.2493 in), and the first diameter 1750 (FIG. 7B) of the pathway of the dispensing tip is 1.22 mm (0.048 in).

Figure 6A:
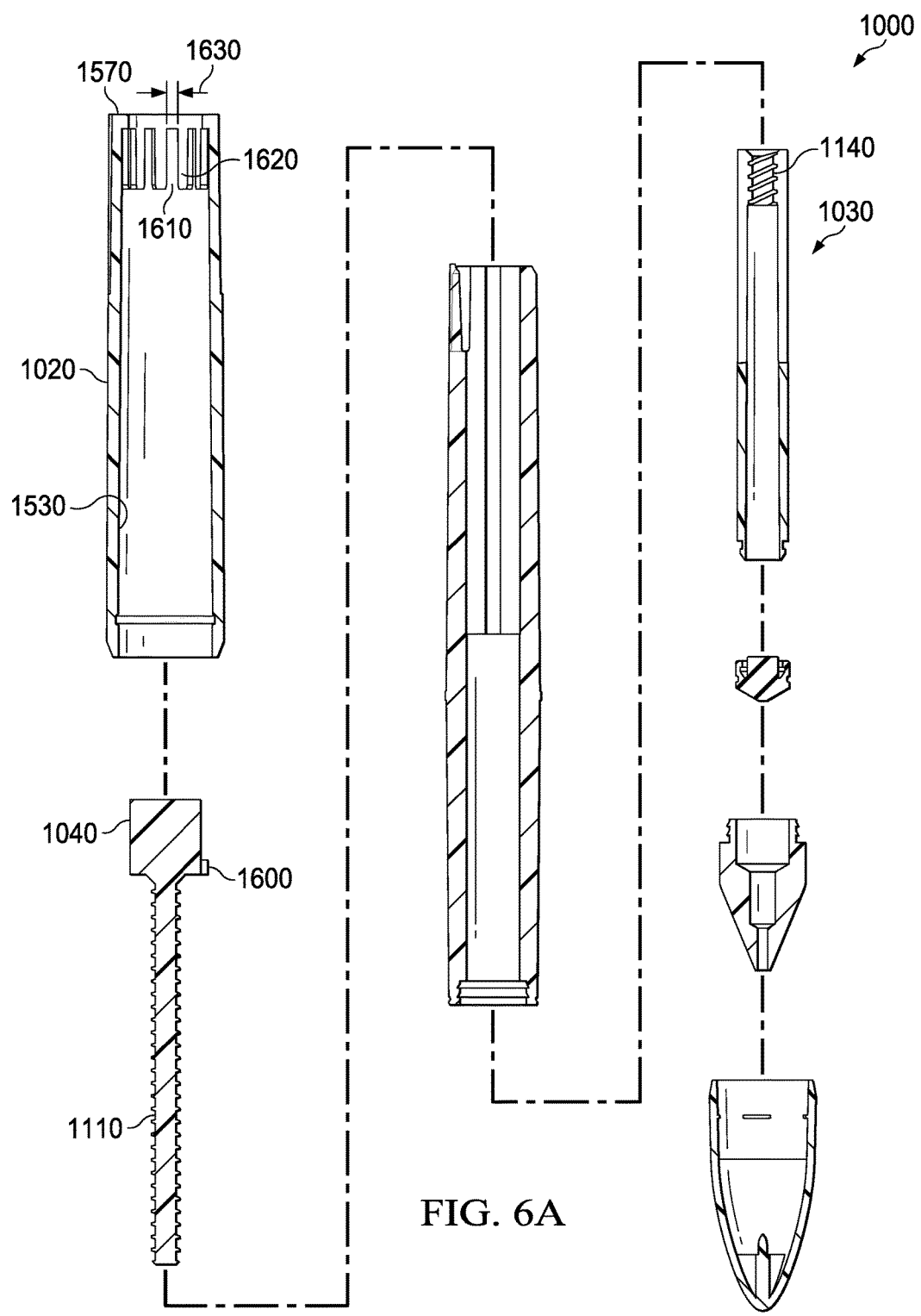

Certain embodiments of a dispensing apparatus 1000, shown in FIG. 6A, comprise features to provide rotational constraint between a push-button 1040 and a twisting sleeve 1020. This rotational constraint translates rotational movement of the twisting sleeve 1020 into rotational movement of the push-button 1040 and thereby the lead-screw 1110 which is connected to the push-button 1040. In such embodiments, the lead screw 1110 interfaces with a female threaded feature 1140 and the rotation of the lead screw 1110 acts to extend or contract a plunger assembly 1030. Such rotational constraint, in certain embodiments, comprises a key 1600 and a keyway 1610. It will be appreciated that a key 1600 and keyway 1610 mating allows for the slidable engagement of two nesting features but limits the rotational movement of the nested features. In such embodiments the push-button 1040 further comprises a key 1600 protruding radially outward from the push-button 1040 and the twisting sleeve 1020 comprises a keyway 1610 within the cylindrical bore 1530 of the twisting sleeve. Such a keyway 1610 is proximal to the second open end 1570 of the twisting sleeve. In such embodiments the keyway 1610 is defined by the distance 1620 between protrusions 1620 extending radially inward from the cylindrical bore 1530. Such protrusions 1620 are typically spaced such that the distance 1630 between the protrusions 1620 allow the slidable engagement of the key 1600 into the keyway 1610 in an axial direction but constrains the key 1600 and keyway 1610 relative to each other rotationally. In will be appreciated that such embodiments are not limited to such configurations and other embodiments may comprise a push-button 1040 with a keyway and a twisting sleeve with a key.

Figure 6B:
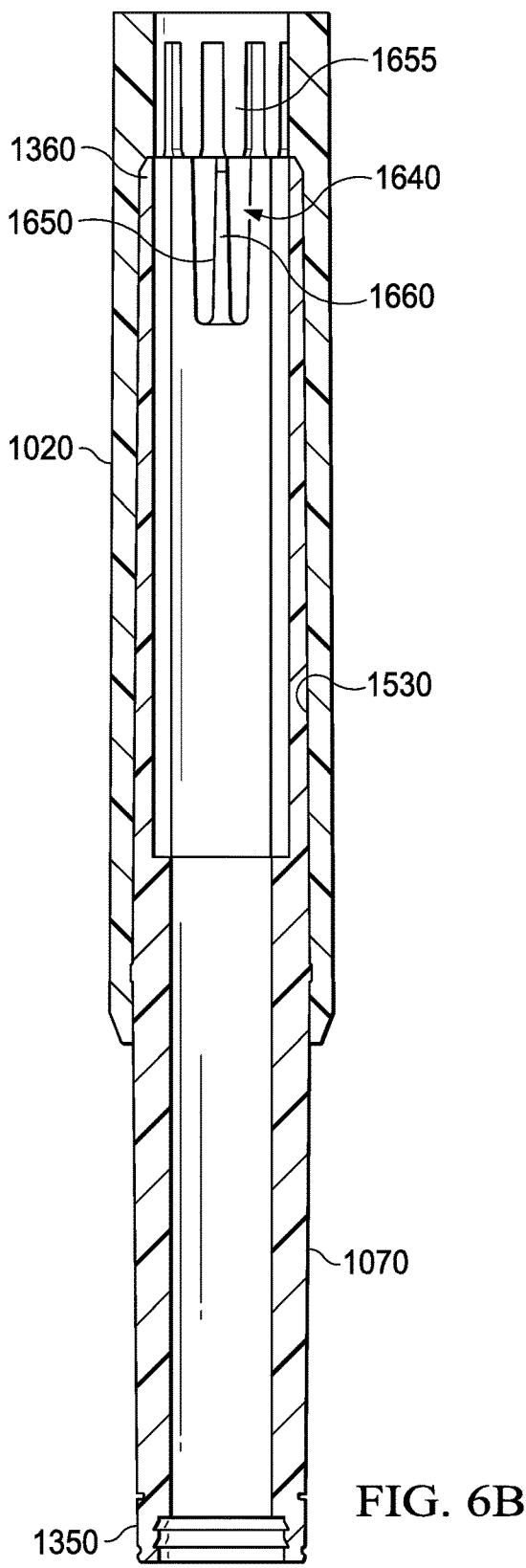

Certain embodiments of a dispensing apparatus 1000, shown in FIG. 6B, comprise a twisting sleeve 1020 and a chamber body 1070 further comprises a clicker device 1640. A clicker device 1640 in such embodiments provides audible and/or tactile feedback with a first clicker element 1650 and a second clicker element 1655 moving rotationally independent from each other. The first clicker element 1650 comprises a flexible or movable feature such that when the second clicker element 1655 traverses past the first clicker element 1650, it deflects the first clicker element 1650. The first clicker element 1650 rebounds to its original position after the second clicker element 1655 has traversed the first clicker element 1650. The rebound of the first clicker element 1650 results in feedback, audible and/or tactile, providing indication of actuation. The feedback may also indicate gradated increments such as volumetric increments. In certain embodiments, the first clicker element 1650 comprises a flexible lever 1660 extending from the second end 1360 of the chamber body and the second clicker element 1655 comprises protrusions 1620 extending from the cylindrical bore 1530 of the twisting sleeve 1020. Interface between the protrusions 1620 and the flexible lever 1660, when the twisting sleeve 1020 is in relation to the chamber body 1070, causes the flexible lever 1660 to deflect and rebound as each protrusion 1620 traverses past the flexible lever 1660.

Certain embodiments of a dispensing apparatus 1000, shown in FIG. 7A, comprise a chamber body 1070, plunger 1100 and dispensing tip 1080 intended for the dispensing of a viscous fluid. The dispensing tip 1080 comprises a first end 1710 where the fluid exits the dispensing apparatus 1000, a second end 1720 which interfaces with the first end 1350 of the chamber body, and a pathway 1730 therebetween. In such embodiments, the dispensing tip 1080 is affixed to the first end 1360 of the chamber body. It will be appreciated that such fixation may be accomplished with threaded features, adhesives or other fixation features known to those skilled in the art. In certain embodiments, such as when a chamber body 1070 comprises a ductile material such as plastic, the fixation of the dispensing tip 1080 to the chamber body 1070 may be accomplished with barbs 1740 proximal to the second end 1720 of the dispensing tip. It will be appreciated to those skilled in the art that a barb 1740 in such an application comprises a feature which allows the insertion of a first element into a second element but makes the extraction of the first element from the second element difficult. In certain embodiments, as shown in FIG. 7A, a barb 1740 comprises an annular feature having a sharp edge protruding radially from the dispensing tip 1700, and the annular feature tapering down as it approaches the second end 1720 of the dispensing tip.

Certain embodiments of a dispensing apparatus 1000, shown in FIG. 7B, comprise a dispensing tip 1080, the dispensing tip 1080 further comprises a pathway 1730 further comprising a first diameter 1750 consistent with the first end 1710 of the dispensing tip, a second diameter 1760 consistent with the first diameter 1750 and disposed between the first end 1710 and the second end 1720 of the dispensing tip, and a third diameter 1770 consistent with the second diameter 1760 and consistent with the second end 1720 of the dispensing tip.

Figures 8A, 8B, 8C:
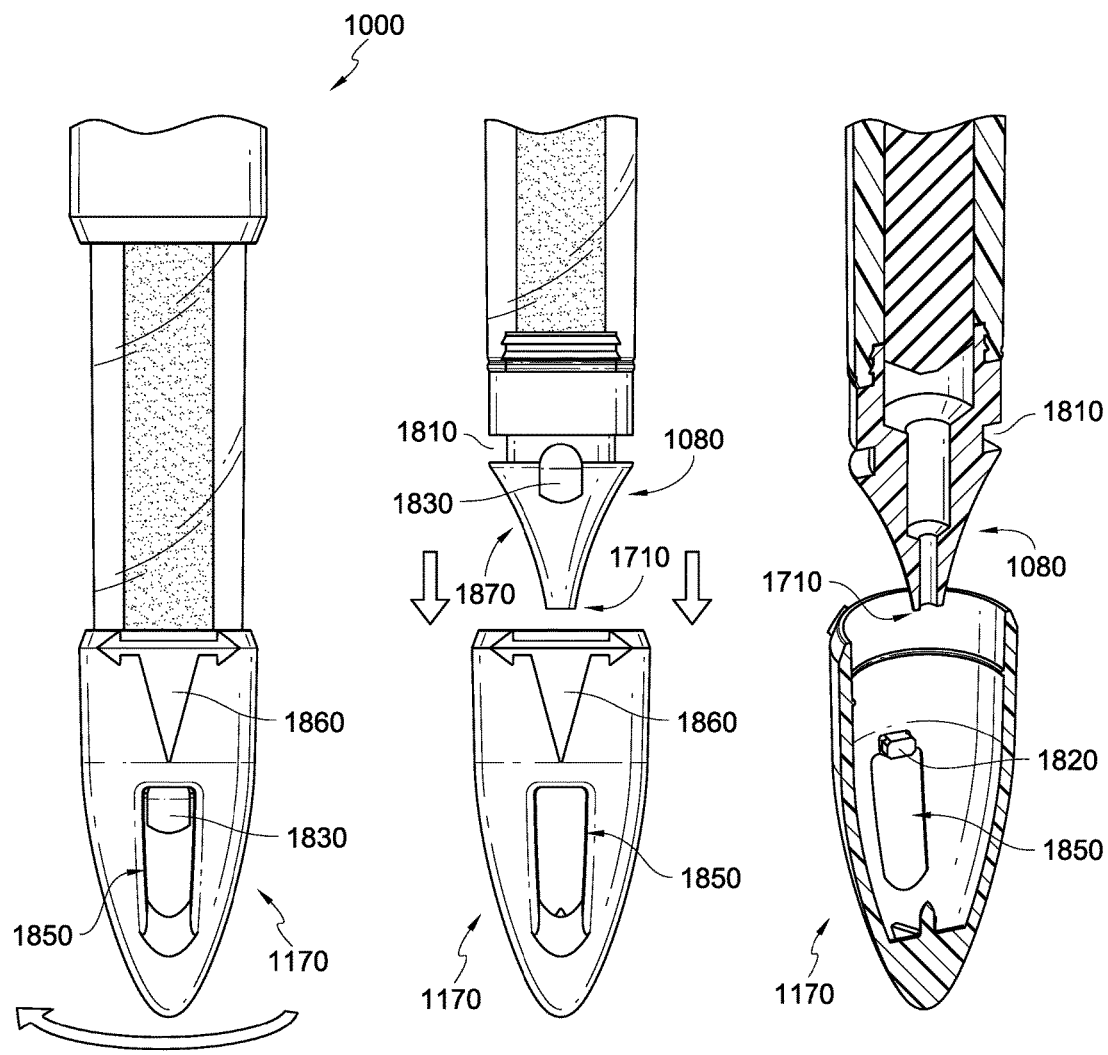

Certain embodiments, as shown in FIGS. 8A-8C for example, comprise a child-safety feature to allow a user to alternatively lock and unlock a cap 1170 to the dispensing tip 1080 of the dispensing device. In certain embodiments, a dispenser tip 1080 further comprises an annular recess 1810 offset from first end 1710 of the dispenser tip. In certain embodiments, the cap 1170 having a child-safety feature further comprises a boss 1820 configured to mate with the annular recess 1810. A child-safety feature of certain embodiments allows a user to alternatively place the dispensing apparatus 1000 in a locked or unlocked configuration.

In certain embodiments, such as FIGS. 8A-8C, which comprise a child-safety feature 1800, the dispenser tip 1080 further comprises a notch 1830 extending from the annular recess 1810 toward the first end 1710 of the dispenser tip wherein the notch 1830 is consistent with an external surface 1840 of the dispenser tip. When the boss 1820 and the notch 1830 are aligned, the boss 1820 can traverse through the notch 1830, into the annular recess 1810. When the cap 1170 is rotated in relation to the dispenser tip 1080, the boss 1820 and the notch 1830 are misaligned, thus locking the cap 1170 to the dispenser tip 1080, thus placing the dispensing apparatus in a locked configuration. When the boss 1820 and the notch 1830 are realigned, thus placing the dispensing apparatus 1000 in an unlocked configuration, the cap 1170 is unlocked from the dispenser tip 1080 and may be removed.

The cap 1170 of certain embodiments, as shown in FIGS. 8A-8C for example, comprises an aperture 1850 through which a user can see a portion of the dispenser tip 1080 with the cap 1170 disposed over the first end 1710 of the dispenser tip. In such embodiments, the boss 1820 is affixed to the cap 1170 in alignment with the aperture 1850. Thus, a user can view through the aperture 1850 to identify the location of the notch 1830 to assist in aligning the boss 1820 with the notch 1830. In certain embodiments, a cap 1170 further comprises indicia 1860 to identify the location of the boss 1820 to assist a user in identifying the location of the boss 1820 in relation to the notch 1830.

Certain embodiments, seen in FIGS. 8B-8C, comprise a dispenser tip 1080 having a concave profile 1870. The concave profile 1870 of the dispenser tip provides a smaller first end 1710 of the dispenser tip with less exposure to build-up of fluid when dispensed.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. The terms "first," "second," "top," "bottom," etc., as used herein, are intended for illustrative purposes only and do not limit the embodiments in any way. Additionally, the term "plurality," as used herein, indicates any number greater than one, either disjunctively or conjunctively, as necessary, up to an infinite number. Further, "Providing" an article or apparatus, as used herein, refers broadly to making the article available or accessible for future actions to be performed on the article, and does not connote that the party providing the article has manufactured, produced, or supplied the article or that the party providing the article has ownership or control of the article. Accordingly, while specific embodiments have been illustrated and described, numerous modifications come to mind without significantly departing from the spirit of the invention and the scope of protection is only limited by the scope of the accompanying Claims.

What is claimed:

1. A dispensing apparatus for the dispensing of fluid comprising:
   a plunger comprising a first end having a plunger tip having a diameter, and a second end of the plunger having a female threaded feature extending through a portion of the plunger toward the first end of the plunger;
   a lead screw having male threading extending from a first end of the lead screw toward a second end of the lead screw, with the male threading configured to engage with the female threaded feature of the plunger;
   the second end of the lead screw affixed to a push-button having a diameter, the push-button further comprises a key having a thickness;
   a chamber body having a hollow form extending from a first end of the chamber body to a second end of the chamber body, an external diameter, and an internal diameter equal to or less than the diameter of the plunger tip;
   a twisting sleeve having a bore comprising a first end having an opening with a diameter larger than the external diameter of the chamber body, and a second end having an opening with a diameter larger than the diameter of the push-button;
   the twisting sleeve further comprising a first protrusion and a second protrusion protruding radially inward from the bore, the protrusions extending from the second end of the twisting sleeve toward the first end of the twisting sleeve, and the protrusions being spaced from each other by a distance greater than the thickness of the key of the push-button; and
   a dispensing tip having a pathway extending between a first end and a second end, the second end of the dispensing tip configured to be affixed to the first end of the chamber body.

2. The dispensing apparatus of claim 1, wherein the plunger further comprises an anti-spin feature comprising a tab feature having a thickness; and the chamber body further comprises a channel extending from the second end of the chamber body toward the first end of the chamber body and terminating therebetween, wherein the channel is configured to mate with the anti-spin feature of the plunger.

3. The dispensing apparatus of claim 1, wherein the plunger further comprises a slot through an external surface of the plunger to an internal surface of the plunger, the slot extends from the second end of the plunger toward the first end of the plunger and terminates therebetween.

4. The dispensing apparatus of claim 1, wherein the male threading of the lead screw comprises thread-steps.

5. The dispensing apparatus of claim 1, wherein the second end of the chamber body further comprises a clicker element comprising a flexible lever extending from the second end of the chamber body, wherein the clicker element interacts with the protrusions of the twisting sleeve when the twisting sleeve rotates in relation to the chamber body, resulting in audible feedback.

6. The dispensing apparatus of claim 1, wherein the pathway comprises, a first diameter extending from the first end of the dispensing tip;

a second diameter adjacent to the first diameter of the pathway;

a third diameter adjacent to the second diameter of the pathway, the third diameter extending to the second end of the dispensing tip, and the third diameter being equal to or less than the maximum diameter of the plunger tip;

the second diameter being less than the third diameter;

and the first diameter being less than the second diameter.

7. The dispensing apparatus of claim 6 further comprising a cap.

8. The dispensing apparatus of claim 7, wherein the cap further comprises an internal stopper configured to mate with the first diameter of the dispensing tip.

9. The dispensing apparatus of claim 7, further comprising a child-safety feature comprising a boss configured to interface with an annular recess of the dispensing tip; and a notch consistent with the annular recess, wherein the interface of the boss with the annular recess and the boss is misaligned with the notch, the cap is in a locked configuration, and wherein the alignment of the boss with the notch results in an unlocked configuration of the cap.

10. The dispensing apparatus of claim 7, wherein the cap further comprises an aperture.

11. The dispensing apparatus of claim 1, wherein the dispensing tip further comprises a fixation feature proximal to the second end of the dispensing tip; and the fixation feature is configured for attaching the dispensing tip to the first end of the chamber body.

12. The dispensing apparatus of claim 11, wherein the fixation feature comprises a plurality of barbs configured for insertion into the first end of the chamber body.

13. A dispensing apparatus for the dispensing of fluid comprising:

a plunger having a hollow form having a consistent cross-sectional profile comprising a first end;

the first end of the plunger having a plunger tip, the plunger tip having a diameter, and a second end of the plunger having a female threaded feature aligned with a central axis of the plunger;

the plunger further comprising an anti-spin feature comprising a tab feature, the tab feature having a thickness;

the female threaded feature extending through a portion of the plunger extending toward the first end of the plunger;

the plunger further comprising a slot through an external surface of the plunger to an internal surface of the plunger and the slot extending from the second end of the plunger toward the first end of the plunger and terminating therebetween;

a lead screw having male threading from a first end of the lead screw extending toward a second end of the lead screw, the male threading configured to engage with the female threaded feature;

the male threading of the lead screw having thread-steps;

the second end of the lead screw having a substantially cylindrical push-button having a diameter, with the push-button further comprising a key, with the key of the push-button having a thickness;

a chamber body having a substantially cylindrical cross-sectional profile and hollow form;

a first portion of the chamber body having an external diameter and an internal diameter equal to or less than the diameter of the plunger tip;

a second portion of the chamber body having a channel having a width equal to or greater than the thickness of the tab features of the plunger, the channel extending from a second end of the chamber body toward the first portion of the chamber body and terminating therebetween; the second end of the chamber body further comprising a first clicker element comprising a flexible lever extending from the second end of the chamber body;

a twisting sleeve having a substantially cylindrical bore, the bore having a first end with an opening having a diameter larger than the external diameter of the chamber body, and a second end of the bore having an opening having a diameter larger than the diameter of the push-button;

the twisting sleeve further comprising a second clicker element comprising a first protrusion and a second protrusion extending from the bore of the twisting sleeve;

the first protrusion and second protrusion extending toward the first end of the twisting sleeve from the second end of the twisting sleeve and the protrusions being separated from each other by a distance greater than the thickness of the key of the push-button;

a dispensing tip having a first end, a second end, and a pathway extending therebetween, the second end of the dispensing tip having a fixation feature for attaching the dispensing tip to a first end of the chamber body;

the pathway comprising a first diameter extending from the first end of the dispensing tip, a second diameter adjacent to the first diameter of the first diameter, and a third diameter adjacent to the second diameter of the pathway, the third diameter extending to the second end of the dispensing tip; and the third diameter being equal to or less than the diameter of the plunger tip, the second diameter being less than the third diameter, and the first diameter being less than the second diameter.

* * * * *